United States Patent [19]
Heldreth

[11] Patent Number: 5,290,313
[45] Date of Patent: Mar. 1, 1994

[54] OFFSET PROSTHETIC STEM EXTENSION

[75] Inventor: Mark A. Heldreth, Mentone, Ind.

[73] Assignee: Zimmer, Inc., Warsaw, Ind.

[21] Appl. No.: 979,978

[22] Filed: Nov. 23, 1992

[51] Int. Cl.⁵ .................................................. A61F 2/38
[52] U.S. Cl. ......................................... 623/20; 623/18
[58] Field of Search ................................ 623/18, 20, 23

[56] References Cited

U.S. PATENT DOCUMENTS

| | | | |
|---|---|---|---|
| 4,790,854 | 12/1988 | Harder et al. | 623/20 |
| 4,822,365 | 4/1989 | Walker et al. | 623/20 |
| 4,822,366 | 4/1989 | Bolesky | 623/20 |
| 4,834,081 | 5/1989 | Van Zile | 128/92 VT |
| 4,936,853 | 6/1990 | Fabian et al. | 623/20 |
| 4,950,297 | 8/1990 | Elloy et al. | 623/20 |
| 4,950,298 | 8/1990 | Gustilo et al. | 623/20 |
| 4,959,071 | 9/1990 | Brown et al. | 623/20 |
| 4,963,155 | 10/1990 | Lazzeri et al. | 623/23 |
| 4,985,037 | 1/1991 | Petersen | 623/20 |
| 5,002,578 | 3/1991 | Luman | 623/23 |
| 5,071,438 | 12/1991 | Jones et al. | 623/18 |
| 5,123,928 | 6/1992 | Moser | 623/20 |
| 5,133,760 | 7/1992 | Petersen et al. | 623/20 |
| 5,133,763 | 7/1992 | Branemark | 623/18 |
| 5,152,796 | 10/1992 | Slamin | 623/20 |

OTHER PUBLICATIONS

Zimmer, Inc.-Catalog pp. A118,A121—Miller/Galante Total Knee—1987 catalog.
Zimmer, Inc.—Catalog pp. A141,A143—MG II Total Knee System—1991 catalog.
Zimmer, Inc.—Catalog pp. A169,A171—Insall/Burstein II Modular Knee System—1991 catalog.

Primary Examiner—David J. Isabella
Assistant Examiner—Debra S. Brittingham
Attorney, Agent, or Firm—Margaret L. Geringer

[57] ABSTRACT

A modular prosthesis system which includes a modular stem extension which has an offset between its attachment point to the prosthesis base portion and the main body of the stem. The stem extension can be attached in a selected orientation with respect to the base portion, thus enabling the main body of the stem to be positioned in any of one of a plurality of orientations with respect to the base portion.

17 Claims, 2 Drawing Sheets

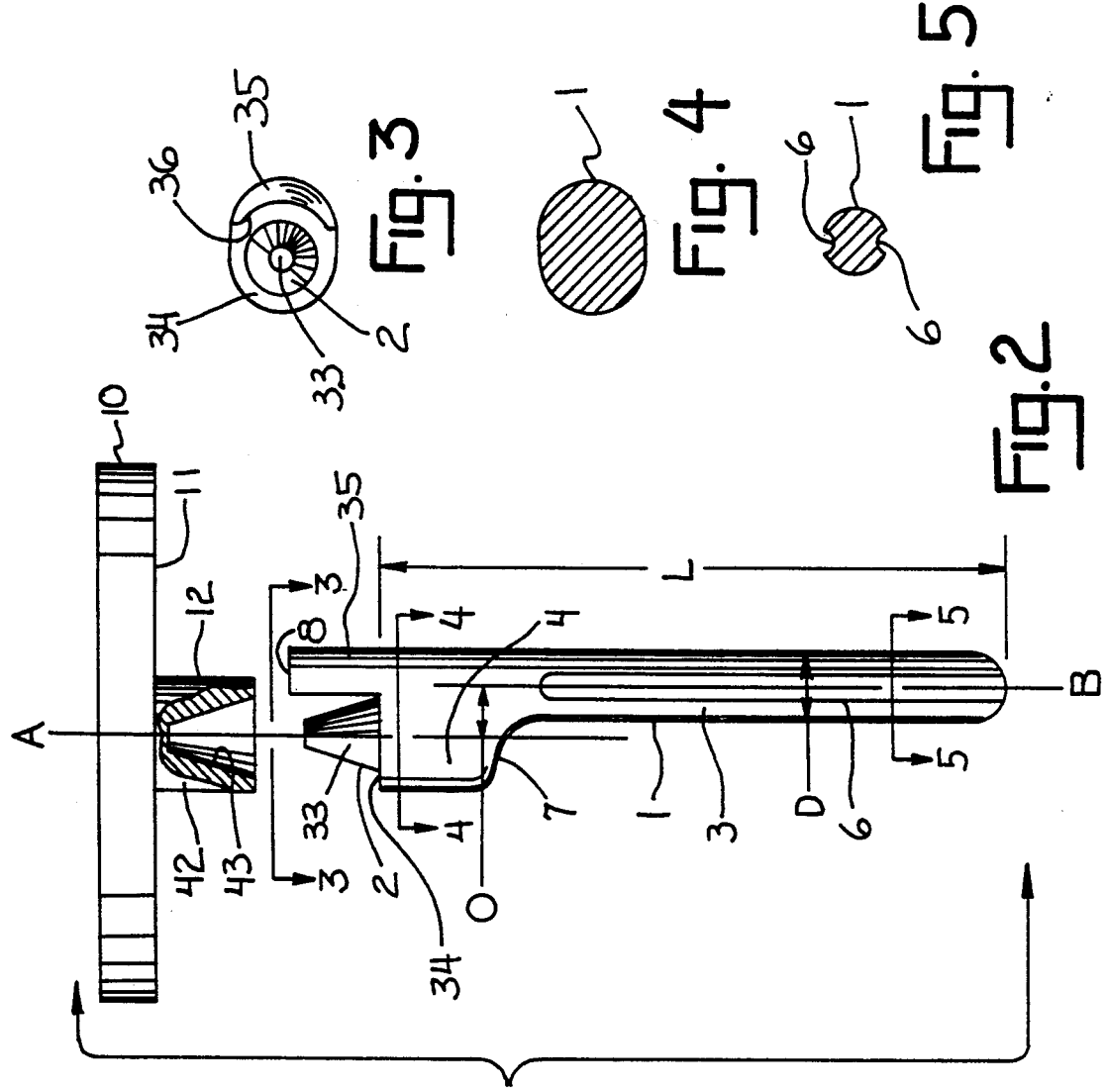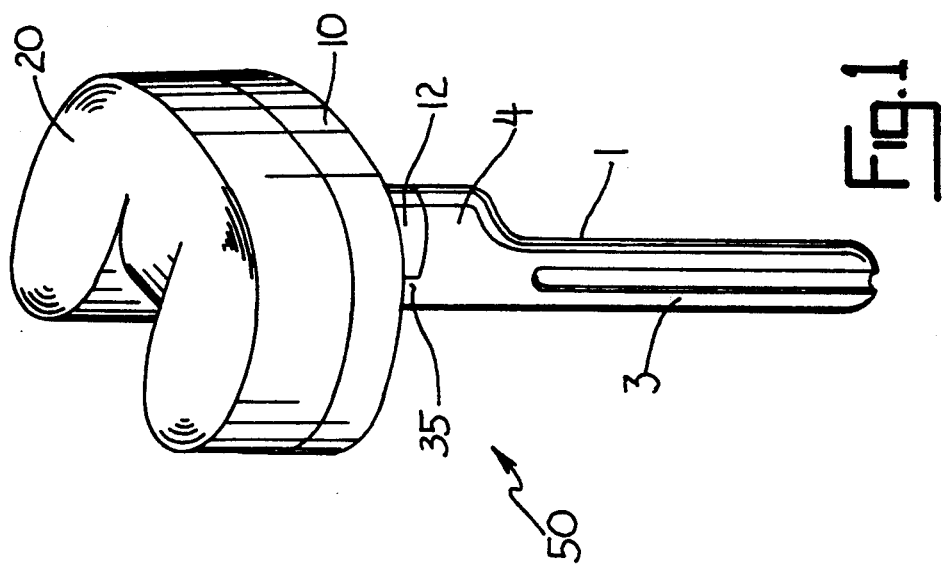

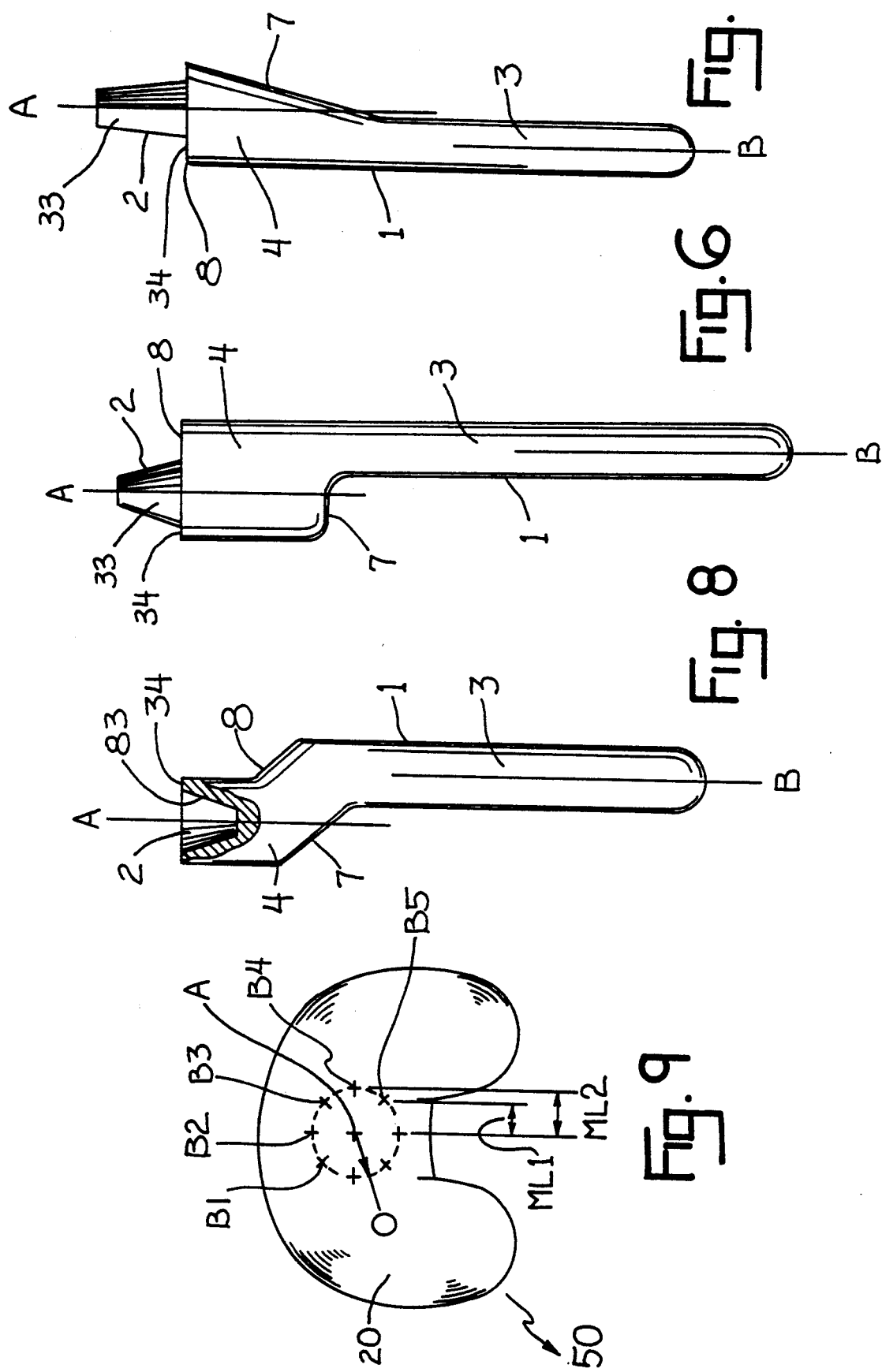

OFFSET PROSTHETIC STEM EXTENSION

BACKGROUND OF THE INVENTION

The present invention relates to a modular prosthetic implant system. In particular, this invention relates to such a system which includes modular stem extensions.

While this invention is particularly suitable for modular tibial prosthesis components having modular stem extensions, the features of this invention could be adapted, as appropriate, to other prosthetic components which utilize modular stem components.

It is well known in the art to utilize modular stem extensions. The following patents disclose the use of modular stem extensions which are straight and aligned with the attachment mechanism: U.S. Pat. Nos. 4,936,853; 4,950,298; and 4,959,071, while U.S. Pat. No. 4,822,366 discloses both a straight modular stem and a modular stem having a bowed or curved end portion.

In addition, U.S. Pat. No. 4,834,081 discloses a modular stem extension which is angled realtive to the prosthesis; while the following patents each disclose modular stems in which the modular angled stem can be attached to the prosthesis base in a plurality of positions to selectively vary the orientation of the angled stem relative to the prosthesis base: U.S. Pat. Nos. 4,822,365; 4,985,037; 5,133,760; 5,152,796.

In addition, U.S. Pat. No. 4,950,297 is noted of related interest. It discloses a control peg 21 which is fitted between the tibial and meniscal components. The control peg includes superior and inferior axial portions which are connected by a collar and are laterally offset from each other. The control peg controls subluxation and/or rotation of the meniscal component with respect to the tibial component. This patent is cited to point out the offset relationship of the control peg. However, it is noted that the control peg of this patent is not a stem extension, and it is utilized in a different manner and for a different purpose than the offset stem extension of the present invention.

OBJECTS OF THE INVENTION

A principal object of this invention is to provide a modular stem extension which has an offset between its attachement point to the prosthesis base portion and the main body of the stem.

A further object of the invention is to provide such an offset stem extension which can be attached in a selected orientation with respect to the base portion, thus enabling the main body of the stem to be positioned in any one of a plurality of orientations with respect to the base portion.

Another object of the invention is to provide a modular stem extension in which the amount of mediolateral offset can be varied depending upon the selected orientation of the stem extension to the base plate.

A still further object of the invention is to provide a modular offset stem extension which can be used with either right or left implant components.

SUMMARY OF THE INVENTION

The present invention provides a modular prosthesis system including a prosthetic base portion and a stem extension which is to be mounted to the undersurface of the base portion. The axis of the main body of the stem or the elongated stem portion of the stem extension is offset or spaced from the axis of the mounting portion of the stem extension.

As noted above, while the features of this invention could be adapted to various stemmed prosthetic components, it is particularly suitable for use with modular tibial prosthesis components, although it is not limited thereto. The anatomy of the human tibia is quite variable with respect to the position of the intramedullary canal relative to the mediolateral edges of the proximal tibia. A stem which is centrally located on the base portion or base plate could interfere with the lateral trbial cortex as a surgeon attempts to center the tibial plate on the proximal cut tibia. There are some patients in which the intramedullary canal is not centrally located relative to the peripheral edges of the proximal tibia. In such cases, the option for an offset stem extension, such as that of the present invention could be a beneficial option. This option could also allow the same base portions or base plates to be used with patients utilizing various styles of stem extensions, including the offset style of the present invention, as well as other known sytles of stem extensions such as straight, bowed, or angled stem extensions.

BRIEF DESCRIPTION OF THE DRAWINGS

These features and objects of the invention, as well as others, will become apparent to those skilled in the art by referring to the accompanying drawings:

FIG. 1 is a perspective view of a modular tibial prosthesis assembly in accordance with the present invention;

FIG. 2 is an exploded front view of the base portion and stem extension of the tibial prosthesis of FIG. 1;

FIG. 3 is a top end view of the stem extension taken along lines 3—3 of FIG. 2;

FIG. 4 is a cross-sectional view of the stem extension taken along lines 4—4 of FIG. 2;

FIG. 5 is a cross-sectional view of the stem extension taken along lines 5—5 of FIG. 2;

FIGS. 6, 7, and 8 are front views of alternate embodiments of the stem extension;

FIG. 9 is a schematic representation of a plurality of various selectable positions of the axis of the stem extension relative to the fixed axis of the mounting or attachment portion.

DETAILED DESCRIPTION OF THE INVENTION

FIGS. 1-9 illustrate particularly advantageous embodiments of the offset prosthetic stem extension of the present invention. The invention will be described with reference to a modular prosthetic tibial component 50; however, it is understood that it is not limited thereto.

The modular tibial component of FIG. 1 includes a base plate or base portion 10, with a modular stem extension 1 attached thereto. The base portion also includes an articular surface or additional portion 20 which may also be modular. Such modular additional portions are well known in the art, and as such, this portion 20 may be secured to the base portion by any suitable attachment mechanism. Typically, the articular surface 20 of a tibial component 50 is made of an ultra high molecular weight polyethylene material; however, any suitable material may be used. Accordingly, the base portion 10 and stem extension 1 are typically manufactured from a metal material such as a cobalt-chrome alloy or a titanium alloy; however, any suitable material may be utilized. Also, any appropriate manufacturing methods may be utilized for these parts.

As seen in FIGS. 2-5, the base portion 10 has an undersurface 11 with a base mounting portion 12 thereon. The stem extension 1 has a stem mounting portion 2 for mounting the stem extension 1 to the base mounting portion 12. The stem extension 1 also includes an elongated stem portion 3 connected to the stem mounting portion 2 by a connecting portion 4. The stem mounting portion has a first axis "A" and the stem portion 3 has a second axis "B" which is substantially parallel to the first axis "A," but which is spaced apart therefrom to provide a fixed offset "O" or fixed distance between the parallel axes "A" and "B."

The stem mounting portion 2 is radially adjustable in cooperation with the base mounting portion 12, so that the second axis "B" of the elongated stem portion 3 can be oriented in any one of a plurality of radial orientations with respect to the first axis "A." This can be seen by looking at the schematic representation of the tibial component 50 shown in FIG. 9. Axis "A" has a fixed orientation relative to the base portion 10 (which may be attached to additional portion 20), while a plurality of radial orientations for the second axis "B" are shown, such as by "B1," "B2," "B3," "B4," "B5." The surgeon would select the desired position for axis "B" relative to the base portion 10, and then the stem extension 1 can be releasably fixed to the base portion 10 in the selected orientation.

The amount of mediolateral offset (the offset in the mediolateral direction) can be varied depending upon the selected orientation of the stem extension 1 relative to the base plate 10. For example, as shown in FIG. 9, if the location for the second axis is "B5," the mediolateral offset would be "ML1," while if the location for the second axis is "B4,"the mediolateral offset would be "ML2" which is a greater mediolateral offset than "ML1." Thus, for a given stem extension 1, while the offset "O" or the actual distance between the axes "A" and "B" is fixed or constant, the mediolaterial offset may vary as the orientation of axis "B" varies relative to the base portion 20 and fixed axis "A." The mediolateral offset may preferably be about 3 to 7 mm, although other offset distances may be selected, as desired.

The base mounting portion 12 may include an extension member 42 with a recess 43 therein. The stem mounting portion 2 includes an extending pin 33 for mating with recess 43. The recess 43 and pin 33 may each include mating tapered or conical surfaces to provide a secure mating interlock therebetween. This conical attachment enables the stem extension 1 to be attached in any selected radial orientation. Also, additional securing features could be utilized to further secure this tapered connection, such as a screw (not shown) which could connect through the base portion 10 into the pin 33 of the stem extension 1. Such screws are known in the art to be used on existing straight stem extensions. It is noted that other suitable attachment mechanisms could be utilized. For example, the attachment mechanism could be keyed (not shown) to provide a specific limited number of relative stem positions rather than the unlimited number of radial positions possible with the smooth conical surfaces shown.

The pin 33 extends from a platform 34 on stem extension 1. As shown in the embodiment of FIG. 2 and 3, a raised wall 35 is spaced apart from pin 33. The extension member 42 extending from undersurface 11 of base portion 10 has a generally cylindrical outer surface. The raised wall 35 on stem extension 1 has a generally curved inner surface 36 to complement the outer surface of the extension member 42. Raised wall 35 partially surrounds extension member 42 when the stem extension 1 is connected to the base portion 10.

Alternate embodiments of extension members 1 are shown in FIGS. 6,7, and 8. For example, while the stem extension of FIG. 2 includes raised wall 35, the embodiments of FIGS. 6,7, and 8 do not. Thus, with the embodiment of FIG. 2 there would be no unfilled space directly above the platform 34 when the stem extension is connected to base portion 10. In comparison, when the embodiment of FIG. 6 is attached to base portion 10, a space directly above the platform 34 (which is not covered by extension member 42) and below undersurface 11 would potentially need to be filled with bone chips or bone grafting material to fill this space, since use of typical surgical procedures would call for reaming or rasping or tamping a suitably shaped hole in the bone to accommodate the correspondingly shaped stem extension 1.

It is noted that the embodiments of FIGS. 6 and 7 are the current preferred embodiments of the present invention. However, the embodiments of FIGS. 2 and 8 are also suitable alternatives. It is understood that other variations in design could be comtemplated in keeping with the features of the present invention.

As shown in FIGS. 1,2, and 5, flutes 6 may be provided in the elongated stem portion, if desired.

As shown in the embodiment of FIG. 8, the stem mounting portion 2 may utilize a conical recess 83 rather than the extending pin 33 of the embodiments of FIGS. 2,6, and 7. When the stem mounting portion is a conical recess 83 as in FIG. 8, then the corresponding base mounting portion would be a conical pin (not shown) extending from the undersurface 11 of base portion 10.

Also, the connecting portion 4 includes a lower transition surface 7 and an upper transition surface 8. The contours of these upper and lower transition surfaces vary with the shape of the connecting portion 4. For example, in the embodiment of FIG. 8, the upper transition surface 8 provides a cutout portion positioned in line above the elongated stem portion. When using such an embodiment in surgery, this cutout portion would need to be filled with bone chips or bone grafting material to fill this space in the bone opening. Alternatively, the upper transition portion 8 of FIGS. 2,6, and 7 extends the connecting portion to fill in the area positioned in line above the elongated stem portion. In FIG. 6 and 7, this upper transition portion 8 is a planar extension of the platform 34, while in FIG. 2 this upper transition portion includes the raised wall 35. As previously mentioned, the embodiment of FIG. 6 will likely require the use of a bone filler material in the space directly above the platform that is not covered by the extension member 42 when the components are interconnected. FIG. 7 may also require such filler material.

The lower transition surface 7 of the connecting portion 4 may typically cross first axis "A." It may cross axis "A" substantially perpendicularly, as shown in FIG. 6, or it may cross it at an angle as shown in FIGS. 7 and 8. Such angle may be between about 5 and 90 degrees, as desired. Alternatively, the lower transition surface 7 may bne a curved surface which crosses axis "A," as shown in FIG. 2.

This modular prosthesis system may include a plurality of base portions of varying sizes and a plurality of stem extensions of varying sizes, such that any one of the stem extensions can be selectively attached to any one of the base portions. The plurality of stem extensions may be sized to provide a plurality of different offsets "0" between the first and second axes "A" and "B." This difference may suitably be a different radial distance or radial offset "0" between axes "A" and "B," as desired. Also, stem extensions 1 may be provided with various stem lengths "L" or various diameters "D," as desired.

While this invention has been described in terms of various particularly advantageous embodiments, those skilled in the art can appreciate that modifications can be made without departing from the spirit and scope of this invention.

I claim:

1. A modular prosthesis system comprising a prosthetic base portion having a surface for positioning adjacent to a corresponding bone, the base portion having a base mounting means thereon, and a stem extension for insertion into a cavity in a bone, the stem extension having a stem mounting means for mounting the stem extension to the base mounting means, and the stem extension further having an elongated stem portion connected to the stem mounting means by a connection portion, and wherein the stem mounting means has a first central longitudinal axis and the elongated stem portion has a second central longitudinal axis substantially parallel to the first axis, but which is spaced apart therefrom to provide an offset therebetween.

2. The system of claim 1 wherein the stem mounting means is radially adjustable in cooperation with the base mounting means so that the second axis of the elongated stem portion can be oriented in any one of a plurality of radial orientations with respect to the first axis.

3. The system of claim 2 wherein the stem extension is releasably fixed to the base portion in the selected orientation.

4. The system of claim 1 wherein the connecting portion includes a lower transition surface which crosses the first axis.

5. The system of claim 4 wherein the lower transition surface crosses the first axis substantially perpendicularly.

6. The system of claim 4 wherein the lower transition surface crosses the first axis at an angle which is between about 5 and 90 degrees.

7. The system of claim 4 wherein the lower transition surface is a curved surface which crosses the first axis.

8. The system of claim 1 wherein the base mounting means includes a recess therein, and wherein the stem mounting means includes an extending pin for mating with the recess.

9. The system of claim 8 wherein the recess and the pin each include mating tapered surfaces to provide a secure mating interlock therebetween.

10. The system of claim 8 wherein the pin extends from a platform on the stem extension and wherein a raised wall also extends from the platform, such that the raised wall is spaced apart from the pin.

11. The system of claim 10 wherein the recess in the base mounting means is formed in an extension member on the base portion and wherein the extension member has a generally cylindrical outer surface and wherein the raised wall on the stem extension has a generally curved inner surface to complement the outer surface of the extension member and which partially surrounds the extension member when the stem extension is connected to the base portion.

12. The system of claim 1 wherein the base mounting means includes an extending pin, and wherein the stem mounting means includes a recess therein for mating with the pin.

13. The system of claim 1 wherein the system includes a plurality of base portions of varying sizes and a plurality of stem extensions of varying sizes, such that any one of the stem extensions can be selectively attached to any one of the base portions.

14. The system of claim 13 wherein the plurality of stem extensions are sized to provide a plurality of different offsets by varying the distance between the first and second axes.

15. The system of claim 1 wherein the connecting portion includes an upper transition surface which provides a cut-out portion positioned axially above the elongated stem portion.

16. The system of claim 1 wherein the connecting portion includes an upper transition portion which extends the connecting portion to at least partially fill an area positioned axially above the elongated stem portion.

17. The system of claim 1 wherein the stem mounting means is selectively positionable in a plurality of orientations with respect to the base mounting means, so that the second axis can be selectively oriented in a plurality of positions with respect to the first axis and with respect to the base portion.

* * * * *